United States Patent [19]

Willett et al.

[11] 3,956,485

[45] May 11, 1976

[54] HATCHING AGENT FOR SUGAR BEET NEMATODE

[75] Inventors: James D. Willett, Moscow; Luther Michael Cheek, Genesee, both of Idaho

[73] Assignee: Research Corporation, New York, N.Y.

[22] Filed: Feb. 15, 1974

[21] Appl. No.: 442,857

[52] U.S. Cl. .............................................. 424/195
[51] Int. Cl.² ...................... A01N 9/02; A01N 9/08
[58] Field of Search ..................................... 424/195

[56] References Cited
OTHER PUBLICATIONS

Wallace, Ann. App. Biol., 44, 274–282 (1956).
Chemical Abstracts, Vol. 75 (1971), p. 109169m.

*Primary Examiner*—V. D. Turner
*Attorney, Agent, or Firm*—Cooper, Dunham, Clark, Griffin & Moran

[57] ABSTRACT

A neutral lipid fraction derived from sugar beet, such as the seedlings of *Beta vulgaris*, or from sugar beet exudate has been found to be an effective hatching agent for the cysts and eggs of sugar beet nematodes.

4 Claims, 2 Drawing Figures

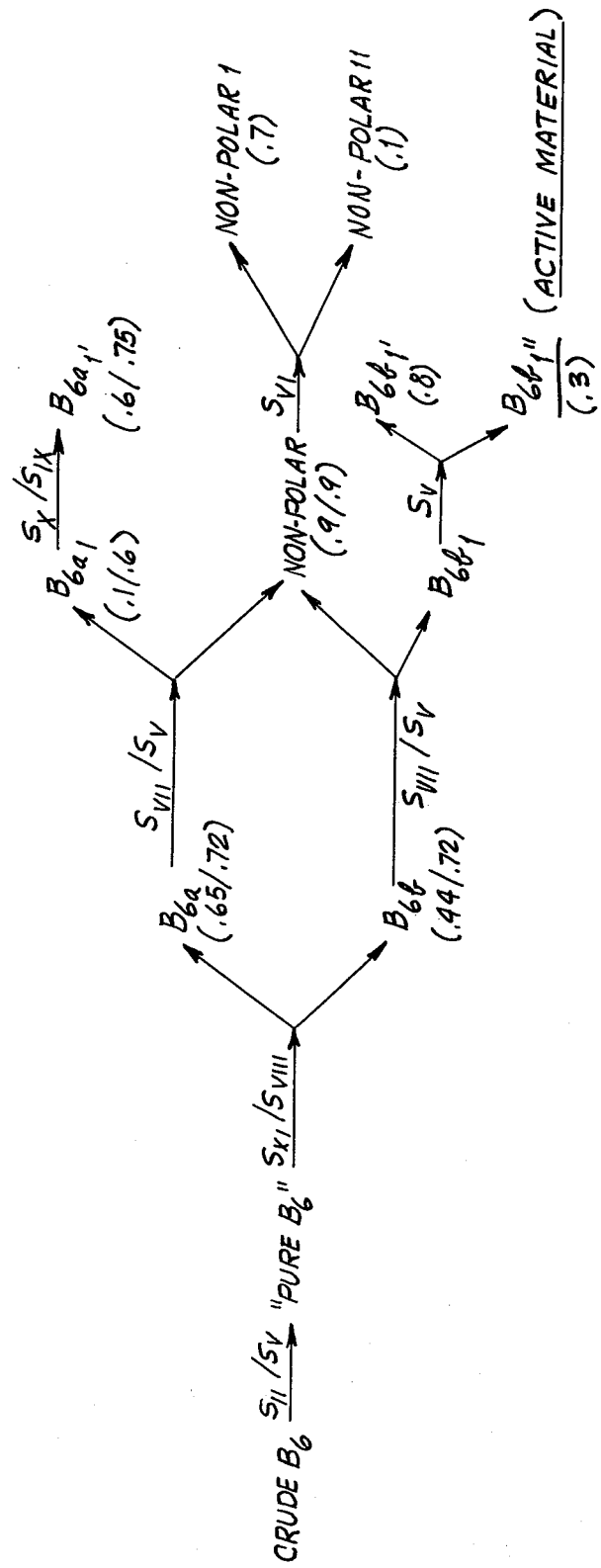

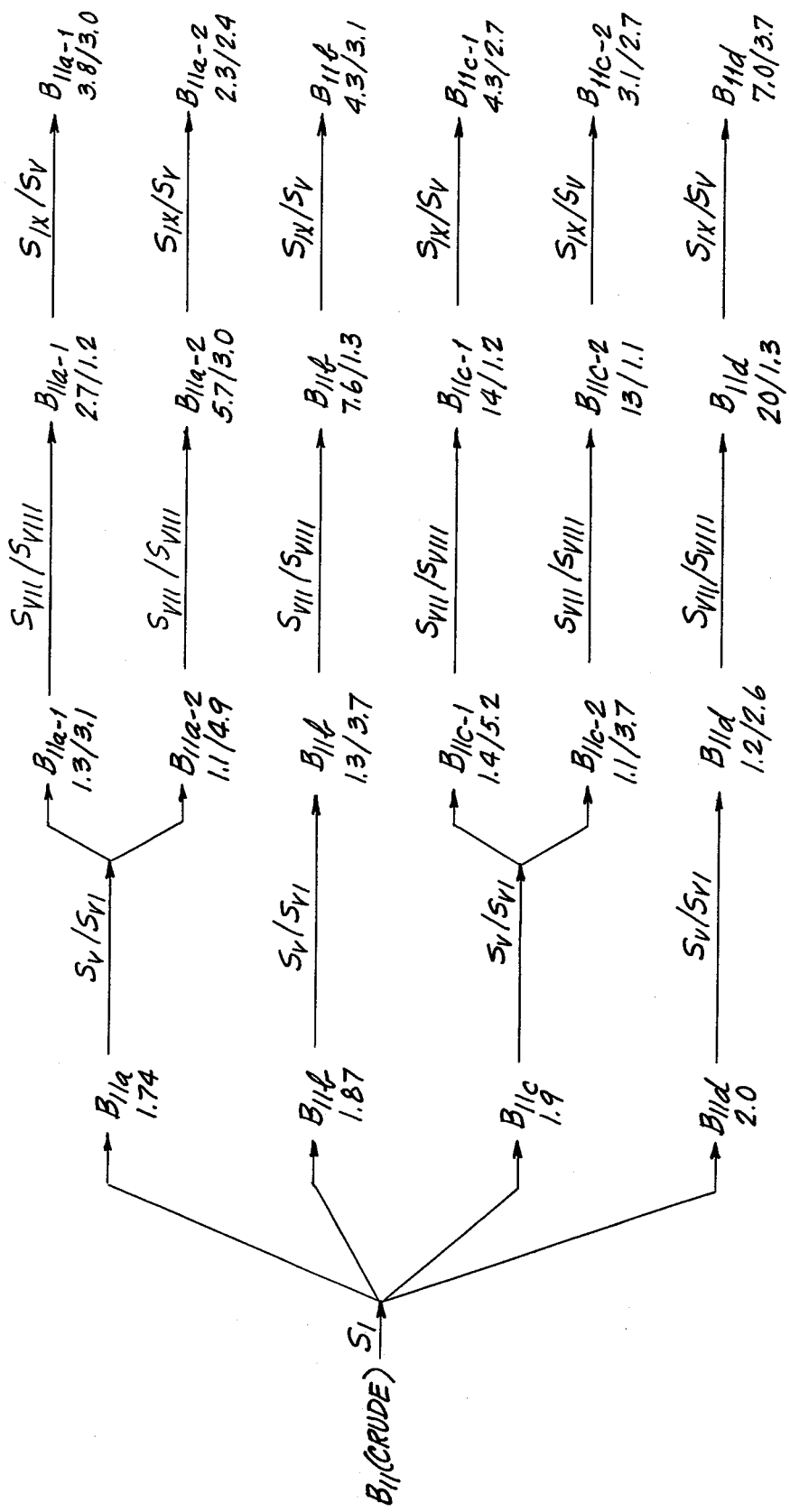

HATCHING AGENT FOR SUGAR BEET NEMATODE

Nematodes, such as the nematode *Heterodera schachtii*, commonly known as the "sugar beet cyst nematode", are a troublesome pest in the growing of sugar beets. The economic loss in sugar beet production throughout the world caused by the sugar beet cyst nematode is enormous.

Plant parasitic nematodes of the genus Heterodera are characterized by the formation of a cyst stage during the course of their normal life cycle. The cyst consists of the hardened body wall of the dead fertile female nematode. The fertilized female deposits a portion of her eggs prior to death but a large number of viable eggs are retained within the body cavity at the time of death. After the female has expired the body casing undergoes a series of chemical changes. These changes result in the tanning of the cuticle of the female resulting in a leathery casing which surrounds the eggs. This cyst now serves as a protective covering for the egg mass contained therewithin. The effectiveness of this protective casing is readily seen when one realizes that the cyst contents of some species of Heterodera have remained viable in soil for periods as long as 8 years. It is this cyst casing, along with the egg casings themselves, which serves to protect the first stage larvae within the cyst from external chemical agents.

The sugar beet cyst nematode produces a cyst holding about 100-1000 eggs. Upon the planting of the sugar beet, such as during the spring, in the presence of sugar beet seedlings the cyst hatches. It appears that some agent or factor generated by the sugar beet plant initiates the hatching of the cyst. The resulting newly hatched nematodes then infect the growing sugar beet plant and cause damage.

Many chemical agents, all of a substantially toxic nature, have been proposed to control the nematode pests. There is good evidence that the presently employed control agents for *Heterodera schachtii* are acting primarily as nematostats rather than as nematicides. These control agents appear to act by inhibiting hatching rather than by effecting a kill of the nematode larvae contained within the eggs. As presently employed the chemical control agents do not reduce the field population of the nematodes over the entire growing season but rather produce their main effect by reducing the nematode population during the early growth stage of the sugar beet plants. These pesticides appear to bring about this reduction by inhibiting the normal hatch of the nematode population in the soil. Further, the presently employed chemical agents act indiscriminately upon many living insects and the like in the soil, some of which may be natural predators or competitors of the nematode.

It has been proposed to apply hatching agents to the soil to hatch the nematode cyst prematurely, such as just prior to the growing season, so that the first stage larvae contained in the egg are hatched, leave the cyst and die since there is no sugar beet host to support the larvae. Many such agents have been proposed, such as amino acids, sugars and inorganic ions, as well as the water soluble fraction derived from sugar beets and beet root diffusate, see H. R. Wallace "The Emergence of Larvae from Cysts of Beet Eel Worm, *Heterodera schachtii* Schmidt, in Aqueous Solutions of Organic and Inorganic Substances", Ann. App. Biol., 44, 274-282 (1956) and "The Stimulatory Properties of Some Organic Substances on Cysts of the Beet Eel Worm, *Heterodera schachtii* Schmidt." Ann. App. Biol., 45, 251-255 (1957). See also Clarke and Shepherd who tested a very large number of water soluble compounds for hatching activity toward cysts of *Heterodera schachtii*, "Synthetic Hatching Agents for *Heterodera schachtii* Schmidt, and their Mode of Action", Nematologica 10, 431-453 (1964). For the most part, however, the agents employed heretofore as hatching factors or agents for the cyst of the sugar beet cyst nematode have not been completely satisfactory.

Accordingly, it is an object of this invention to provide a material useful as an agent for hatching the cysts of sugar beet nematodes.

It is another object of this invention to provide a technique for combatting nematodes, particularly by prematurely hatching the cysts of sugar beet nematodes.

Still another object of this invention is to provide a method for the production of an agent useful as a hatching agent for sugar beet nematode cysts.

How these and other objects of this invention are accomplished will become apparent in the light of the accompanying disclosure and drawings wherein FIGS. 1 and 2 illustrate flow schemes for the separation of the hatching agents in accordance with this invention. In at least one embodiment of this invention at least one of the foregoing objects will be achieved.

It has been discovered that lipid material or lipid-containing extracts or diffusates derived from cotyledonous plants, such as leafy sugar beet plants, e.g. the seedlings of the sugar beet *Beta vulgaris*, including their root exudates, exhibit hatching activity with respect to the cysts of sugar beet nematodes. The lipid material or fraction exhibiting hatching activity with respect to the nematode cysts is a neutral lipid fraction and the active component appears to be a terpenoid. One neutral lipid fraction prepared in accordance with this invention and exhibiting activity as a hatching agent for nematode cysts has a molecular weight of about 410. Another lipid fraction prepared in accordance with the practice of this invention has a molecular weight of about 255. Another lipid fraction exhibiting activity as a hatching agent for nematode cysts has a molecular weight of about 435.

The lipid materials prepared in accordance with this invention have been found to possess hatching activity with respect to sugar beet nematode cysts, particularly *Heterodera schachtii*. The primary host of the sugar beet cyst nematode is the sugar beet *Beta vulgaris*. Other plants can also serve as hosts for this nematode. For example, *Heterodera schachtii* is known to infest cabbage, rhubarb and red and white clover. Some field weeds have also been found to serve as suitable hosts for the beet nematode. The following plant families are known to serve as hosts for the beet nematode: Chenopodiacae, Cruciferae, Polygonaceae, Leguminosae, Caryophykaceae, Amaranthaceae and Portulacaceae. The lipid fractions or materials derived from sugar beets and found to be active as a hatching factor for the cyst of *Heterodera schachtii* would also appear to be an effective control agent for this nematode and the hatching factor in any one of the alternate hosts. The lipid fractions and materials of this invention would also appear to be useful to control the closely related plant parasites, *H. glycines* (soybeans), *H. trifolii* (clover), *H. rostochiensis* (potatoes) and *H. avenae* (grain). It would also appear that the lipid materials of this invention would be useful for the control of other nematodes of the genus Heterodera.

The lipid fraction derived from sugar beet material in accordance with this invention can be obtained by macerating sugar beet plants or seedlings and extracting the resulting macerated material with an organic solvent, such as methanol or chloroform or an admixture thereof, e.g. 1:1 mixture. Effective lipid material is also obtainable from young sugar beets, grown asceptically and hydroponically harvested, lyophilized and solvent extracted. The lipid fraction or material evidencing hatching activity is also obtainable by extracting the root exudate of sugar beet hydroponically grown in chemically sterile sand. When obtained in this manner the sand would be separated from the growing sugar beet seedling and extracted with a solvent. Techniques of growing plants in a sterile culture on chemically cleaned sand are known and the technique employed for testing the lipid fraction of root exudate material in accordance with this invention is similar to that used by Viglierchio and Yu "On the Nature of Hatching of Heterodera Schachtii II. Nature Sources of Hatching Stimulants.", J. Amer. Soc. Sugar Beet Technol. 13, 354–361 (1965).

The lipid materials or fractions in accordance with this invention when used as control or hatching agents for the cyst nematode have desirable qualities which are not possessed by conventional pesticides and nematicides. First of all, the lipid materials of this invention are highly specific for the nematode and would not have or be expected to have deleterious effects on other soil organisms or on the plants. Secondly, the use of the lipid materials in accordance with this invention would directly affect the total population of the nematode in the soil and after a series of treatments of the soil with the lipid materials the nematode population could, in principle, be reduced to a level approaching zero. This result does not appear to be possible with present control agents. Thirdly, the lipid materials in accordance with this invention could also be used in combination with conventional pesticides. For example, the lipid materials would stimulate the nematode to hatch in the absence of its host. The soil could then be treated with one of the conventional pesticides which would be effective on the hatched larvae and thus would produce a kill which would have the effect of reducing the soil nematode population.

In the application of the lipid materials for nematode control the lipid materials would be applied prior to the time the soil is seeded, e.g. prior to the sugar beet growing season. The exact time the soil is treated with the lipid material is not critical and, indeed, the lipid material could be applied, if desired, to the soil even during or after the growing season. It is preferred, however, to apply the lipid material to the soil just before the growing season or before the field to be treated is seeded, such as during the spring. The amount of the lipid material, the bulk material or the active component thereof employed to treat the soil would be somewhere in the range between about 20 grams per acre up to 1000 grams per acre, more or less. A single application might be made within the above-indicated dosage range or a number of treatments up to about 3 or 5 or more, if desirable, may be made prior to and even into the growing season.

In the preparation of the effective lipid materials in accordance with this invention conventional techniques for the separation of neutral lipids from polar lipids are employed. For example, the neutral lipid fraction from the roots, plants or root exudates can be isolated on a large scale by standard column chromatographic techniques using silica gel or other solid support or absorbent suitable for the separation of neutral lipids from polar lipids. For example, lipid materials found to be effective in accordance with this invention can readily be extracted from the roots, leaves and root exudates of Beta vulgaris, the sugar beet. The lipids can be extracted, as indicated hereinabove, by a number of procedures, such as by extraction or contact with liquids or compounds or mixtures known to be solvents for lipids. It has been observed that in all cases the hatching activity is associated with the extracted neutral lipids.

Described hereinafter are a number of procedures carried out to demonstrate the practices of this invention and the effectiveness of the special neutral lipid materials as hatching agents for sugar beet nematodes and the like. All extractions of the total lipids from the beets and beet root exudates were carried out by the method of Folch et al *J. Biol. Chem.* 226, 497 (1957). Preliminary separation of the isolated total lipids was carried out by thin layer chromatograph (TLC) using the solvent system of Skipski et al, *Biochim.Biophys. Acta*, 106, 386 (1965) for the separation of neutral lipids from polar lipids. Repeated biological tests of the polar lipids isolated from the lipids of either the beet or of the beet root exudates never gave any evidence of any hatching activity. All activity toward hatch of the cyst contents, e.g. cysts of *H. schachtii*, was found in the groups of the neutral lipid material isolated.

The original assays of the neutral lipid materials or fractions were carried out on material isolated from 1-cm bands removed consecutively from 20-cm plates run in the Skipski solvent system. Significant biological activity was found associated with material isolated at about the 6-cm (hereinafter called B-6 material) and 11-cm (hereinafter called B-11 material) regions of the plate when the solvent front was stopped at 16-cm. The B-6 and B-11 materials have $R_f$ values of 0.38 and 0.67, respectively. Neither of these $R_f$ regions corresponds to $R_f$ values representative of any of the standard lipid classes. Other solvent systems normally used to identify neutral lipid classes, B. W. Nichols, *Biochim. Biophys. Acta* 70, 417 (1963) were employed for the corresponding B-6 and B-11 materials or the respective active regions in such systems and it was found that these materials do not belong to any readily identifiable neutral lipid class. The B-6 material falls in the general region for sterols but runs appreciably faster than any of the standard $C_{27}$ or $C_{30}$ sterols and triterpenes. The B-11 material runs near the region characteristic of fatty acids, sterol esters and triglycerides but could not be co-chromatographed with any of the standards used.

The active lipid materials, the B-6 fraction and the B-11 fraction, were analyzed. The B-6 material was found to contain two major components, one with a molecular weight of 410 and with an NMR spectrum indicating the material to be a terpenoid and the other with a molecular weight of about 255. Another material present in a much smaller amount in the B-6 material had a molecular weight of about 435 and also appeared to be a terpenoid material.

The B-11 material, like the B-6 material, shows activity toward hatch of the eggs in the cyst of *H. schachtii* but is not as active as the B-6 material. The B-11 material is more complex than the B-6 material. The B-11 material contains at least 5 distinct components. Using the "hatching rating" ($H_r$) or Clarke and Shepherd supra and applying this rating to the mean hatch responses shown by the B-6 and B-11 materials, the B-11 neutral lipid materials had an $H_r$ of 304 and the B-6 neutral lipid material had an $H_r$ of 596. Since these are mean ratings, these ratings do not represent the highest values obtained. The highest hatching ratings ever obtained heretofore have been obtained on high concentrations or organic acids and dyes in the range 10 mM and even at these concentrations $H_r$ values have never been greater than 300.

The responsiveness of the cyst Heterodera to hatch is known to be a function of pH and in all cases in the literature where a substance is shown to have a high rating it is generally the case that the substance or compound is acidic. The hatching ratings obtained with the active B-6 and B-11 neutral lipid materials were all obtained near neutrality or about pH 7. Further, the lipid materials of this invention are active at a far lower concentration than any other materials previously tested. It is therefore apparent that the B-6 and B-11 materials of this invention posses high and very specific activity with respect to the hatch of the eggs (and cysts) of the plant parasitic nematode H. schachtii.

In one technique for the recovery of the lipids exhibiting hatching activity seedlings were grown hydroponically under asceptic conditions in all glass growth chambers. The beets were grown in white Delmonte sand which had been washed in concentrated $HNO_3$, backwashed with water until the water washes were neutral and then extracted with acetone for three days and finally extracted with $CHCl_3$ for three days. The sand was added to clean growth chambers and the entire unit sterilized in an autoclave for 30 minutes. The seeds were sterilized with 25% Clorox (v/v) and washed repeatedly with sterile distilled water. The aqueous nutrient employed was that of Meyer et al "Introduction to Plant Physiology", p. 324, published D. Van Nostrand Co., Princeton, New Jersey (1963) and was prepared with sterile distilled Millipore-filtered water and then autoclaved prior to use. The nutrient solution was added when the seeds were planted and the process repeated as necessary to insure good growth of the seedlings.

The exudate was removed for the first time after the plants had germinated and exudate was collected continually until the plants were 6 weeks old. The exudate was collected on alternate days from eight growth chambers and amounted to a total volume of 500 to 1000 ml, depending upon the amount of sand used in the chambers. The total combined exudates from the chambers was filtered through glass fiber paper and the water removed in vacuo. THe residue (0.4 g) was extracted with 200–300 ml of 2/1 (v/v) $CHCl_3/CH_3OH$. The organic extract was filtered through a fine to medium fritted sintered glass funnel and the solvents removed in vacuo. The residue (20 mg) contained the total lipids from the exudate and was stored immediately under an atmosphere of $N_2$ in the cold. When sufficient material (150–200 mg) was collected, the total lipids were combined and washed as described by Folch et al (1957).

For the fractionation of the recovered lipid materials by thin layer chromatography (TLC) a number of solvent systems are available. Suitable solvent systems are described hereinbelow:

System I. as described by Skipski et al (1965) supra.

System II. This is a modification of the above Skipski et al system in order to avoid the use of acetic acid which is part of the standard Skipski system. The plate is run to one-half of its length with the solvent isopropylether ethylacetate (2% v/v), followed by 90/10 (v/v) petroleum ether-ether.

System III. This is a solvent system which has been used specifically for the separation of the lipid classes from plants, see Nichols, supra.

System IV. This solvent system of Nichols (1963) supra consists of a v/v/v mixture of hexane/ethylacetate/acetic acid (70/30/1).

System V. This solvent system consists of chloroform and 5% ethylacetate.

System VI. This solvent system consists of pure hexane.

System VII. This solvent system consists of benzene and chloroform (10/1, v/v).

System VIII. This solvent system consists of chloroform and acetone (2/1. v/v).

System IX. This solvent system consists of pure chloroform.

System X. This solvent system consists of pure acetone.

System XI. This solvent system consists of pure isopropylether.

System XII. This solvent system consists of isopropylether/acetic acid (96/4, v/v).

System XIII. This solvent system consists of petroleum ether/ethyl ether/acetic acid (90/10/1, v/v/v)

System XIV. This solvent system consists of petroleum ether/ether (90/10, v/v).

System XV. This solvent system consists of toluene/1,2-dichloroethane (90/10, v/v).

Separations by TLC were effected using a variety of solvent systems and, in most cases, two-dimensional TLC was used as it appears to give better resolution of the several components and eliminates one step involving removal of the components from the TLC plates.

The lipid materials identified as B-6 can be isolated from either the roots of seedlings of Beta vulgaris or from the corresponding plant root exudates. In the case of root exudate, the filtered aqueous solution was concentrated in vacuo at 40°C. and the solid residue extracted by the procedure of Folch et al. The resulting organic phase was concentrated in vacuo to give the total lipid fraction.

A similar procedure was used to extract the total lipids from the beet roots. Extractions in this case were carried out on the freeze-dried beet roots. Concentration of the filtered extracts yielded the beet root total lipid fraction. The total lipid fraction from exudate amounted to 4.5% of the dry weight obtained on concentration of the crude exudate. To obtain 180 mg of total lipid from the exudate required from 3500 to 5600 ml of exudate collected over a period of 14 days. The root lipids comprise 2.5% of the dry weight of the freeze-dried root materials. The root material was collected by cutting away the tops of 4–6 week old beet seedlings. The total lipids from either source, exudate or root, contained active hatching agent. The B-6 region showed very little difference in the number of components obtained; however, this was not the case for B-11 material isolated from the sources. Both contain the active components but in the case of B-11 material from the beet root lipids, there are several components which were not present in the exudate material. The lipid materials B-6 and B-11 show the typical activity toward hatch of the cyst contents of *H. schachtii* whether isolated from the roots or from the exudate. The lipids B-6 and B-11 show similar TLC behavior whether isolated from the roots or from the exudate and show identical mass spectral fragmentation patterns.

To obtain B-6 and B-11 materials, the isolated total lipids are subjected to TLC using either solvent System I or solvent System II. The initial separations of these bands are carried out on 500-μ TLC plates using silica gel G as the absorbent. The neutral lipids comprise some 55% of the crude total lipids, and B-6 represents approximately 3.5% of the total lipids isolated. Further resolution of B-6 into its individual components involves the application of a series of two-dimensional TLC solvent systems. The $R_f$ values for these systems are reported as follows: $R_f$ (first solvent system)/$R_f$ (second solvent system). Thus, a component separated in two solvent systems run two-dimensionally, each showing an $R_f$ value of 0.5, would be assigned an $R_f$ value of 0.5/0.5.

The material from Band 6 has been resolved into five separate components, which give single spots on repetitive TLC. The flow diagram, FIG. 1 of the drawings, illustrates the fractionation of the B-6 lipid material. Two of the resulting components, nonpolar I and II, are very nonpolar and seem to be the same material or at least highly similar materials.

Only one of the components isolated from B-6 has shown biological activity. The material labeled "$B_{6b-1}$" in FIG. 1 has been tested at a concentration of $7 \times 10^{-6}$, where it has a hatching rating ($H_r$) or 600. None of the other materials derived from B-6 lipid material has shown any appreciable activity. That this same active material is present in both the B-6 root material and the B-6 exudate material was determined by comparing the mass spectra obtained on the active material from each.

The B-11 material, about 7% of the total lipids extracted, can be isolated from either the roots of the *Beta vulgaris* seedlings or from the plant root exudates. The total lipids from either source, isolated as described hereinabove, were subjected to TLC using solvent Systems I and II. Application of these two solvent systems in a two-dimensional fashion separates B-11 into four major spots, two of which can be resolved into two components each, see the flow diagram of FIG. 2 of the drawings which illustrates the fractionation of the B-11 lipid material. The comparison of B-11 material from the root exudate with B-11 material from the extracts of the roots themselves shows the roots to contain 14 components. Of these 14 components, three have been shown to be identical both chromatographically and by mass spectroscopy to components present in the exudate. These three components correspond to $B_{11c-1}$, $B_{11c-2}$ and $B_{11b}$ of FIG. 2. Since hatching activity has been observed from B-11 material isolated from both the roots and from the exudate, the three components found to be common to both $B_{11c-1}$, $B_{11c-2}$ and $B_{11b}$ appear to be the components possessing hatching activity.

Hatching experiments were carried out to demonstrate the effectiveness of the lipid materials of this invention. The tests included 6 control groups (water, exudate, 0.1 mM $ZnCl_1$, viscous root material, Tween-80 and HC) and 4 lipid fractions, B-5, 7, 11 and 13. Each group comprises three (Tween 80) or five (all other groups) nematode dishes, each containing 100 cysts. The cysts were maintained at room temperature. After a presoaking period, the appropriate test solution was added to each dish. Every 2–3 days for about 2 weeks thereafter, the solution was removed from each dish, the cysts were rinsed with Millipore-filtered distilled water, and the solution and rinse water were examined for the presence of larvae. The cysts were then exposed to 3% $H_2O_2$ for about 1 minute and washed three times with Millipore-filtered distilled water. After the third wash, the aqueous test solution having a concentration of the component tested not greater than 1 mg/ml was added to each dish, and the cysts were exposed to ultraviolet light for 10 to 15 minutes.

Upon completion of the experiment a live-dead count of the eggs and larvae within the cysts was performed. Ten cysts were removed from each group, macerated and treated with 0.5% $KMnO_4$ for 20 minutes. A second set of 10 cysts was removed from each group, macerated and exposed to a 0.05% solution of new blue R (shepherd, 1962) for 6–7 days. In both cases, living eggs and larvae remained colorless or white, whereas dead ones took up the stain. On this basis, the resulting numbers of live and dead eggs and larvae were recorded, see accompanying Table I. For each group, the total number of larvae counted throughout the experiment was divided by the number of live eggs observed in each set of 10 cysts and expressed as a percentage, see accompanying Table II.

TABLE I

| | Water Control[+] | Exudate Control[+] | Live-dead count of 10 cysts treated with $KMnO_4$ and 10 cysts treated with new blue R | | | | Fraction 5[++] | Fraction 7[+++] | Fraction 11[+++] | Fraction 13[++] |
| | | | 0.1 mM $ZnCl_2$ Control[+] | Viscous Root Control[+++] | Tween 80 Control[+++] | H.C.* Control[+++] | | | | |
|---|---|---|---|---|---|---|---|---|---|---|
| .5% $KMnO_4$ | | | | | | | | | | |
| Live worms | 31 | 28 | 2 | 9 | 23 | 18 | 17 | 75 | 42 | 16 |
| Dead worms | 36 | 32 | 12 | 7 | 14 | 13 | 12 | 45 | 28 | 10 |
| Live eggs | 1429 | 706 | 599 | 583 | 833 | 902 | 817 | 805 | 572 | 579 |
| Dead eggs | 344 | 38 | 114 | 85 | 52 | 107 | 39 | 124 | 73 | 21 |
| .05% new blue R | | | | | | | | | | |
| Live worms | 10 | 39 | 52 | 24 | 53 | 25 | 17 | 20 | 31 | 58 |
| Dead worms | 9 | 12 | 25 | 11 | 6 | 5 | 12 | 20 | 8 | 14 |
| Live eggs | 244 | 877 | 829 | 542 | 583 | 427 | 613 | 528 | 426 | 521 |
| Dead eggs | 1017 | 357 | 310 | 421 | 355 | 486 | 217 | 163 | 134 | 108 |

[+]Little contamination with mold
[++]Moderable contamination with mold
[+++]Much contamination with mold
*H.C. is a general disinfectant for human and veterinary use comprising sodium hypochlorite solution.

TABLE II

| Group | Emerged Larvae | Live Worms 10 cysts | Dead Worms 10 cysts | Total Larvae | Live Eggs | Total Larvae + Live Eggs | % Hatched Larvae total Live Eggs |
|---|---|---|---|---|---|---|---|
| 0.5% $KMnO_4$ | | | | | | | |
| Water control | 8 | 31 | 36 | 75 | 1429 | 1504 | 4.9 |
| Exudate | 30 | 28 | 32 | 90 | 706 | 796 | 11.3 |
| 0.1mM $ZnCl_2$ | 55 | 2 | 12 | 69 | 599 | 668 | 10.3 |
| Viscous root | 29 | 9 | 7 | 45 | 583 | 628 | 7.2 |
| Tween 80 | 25 | 23 | 14 | 62 | 833 | 895 | 6.9 |
| HC | 19 | 18 | 13 | 50 | 902 | 952 | 5.3 |
| Fraction 5 | 19 | 17 | 12 | 48 | 817 | 865 | 5.5 |
| Fraction 7 | 50 | 75 | 45 | 170 | 805 | 975 | 17.4 |
| Fraction 11 | 9 | 42 | 28 | 79 | 572 | 651 | 12.1 |
| Fraction 13 | 29 | 16 | 10 | 55 | 579 | 634 | 8.7 |
| 0.05% New Blue R | | | | | | | |
| Water control | 8 | 10 | 9 | 27 | 244 | 271 | 10.0 |
| Exudate | 30 | 39 | 12 | 81 | 877 | 958 | 8.5 |
| 0.1mM $ZnCl_2$ | 55 | 52 | 25 | 132 | 829 | 961 | 13.7 |
| Viscous root | 29 | 24 | 11 | 64 | 542 | 606 | 10.6 |
| Tween 80 | 25 | 53 | 6 | 84 | 583 | 667 | 12.6 |
| HC | 19 | 25 | 5 | 49 | 427 | 476 | 10.3 |
| Fraction 5 | 19 | 17 | 12 | 48 | 613 | 661 | 7.3 |
| Fraction 7 | 50 | 20 | 20 | 90 | 528 | 618 | 14.6 |
| Fraction 11 | 9 | 31 | 8 | 48 | 426 | 474 | 10.1 |
| Fraction 13 | 29 | 58 | 14 | 101 | 521 | 622 | 16.2 |

Emerged larvae/group, hatched worms and live eggs/set of 10 cysts, and percentage eggs hatched per live eggs for each group As will be apparent to those skilled in the art in the light of the foregoing disclosure, many alterations, modifications and substitutions are possible in the practice of this invention without departing from the spirit or scope thereof.

We claim:

1. A method of controlling the heterodera nematode population in soil suitable for the planting and growing of sugar beets which comprises extracting finely divided or macerated sugar beet with methanol or chloroform or a mixture thereof to dissolve or extract lipid material therefrom, fractionating the resulting extracted lipid material to separate a terpenoid-containing neutral lipid fraction, the terpenoid contained in said neutral lipid fraction having a molecular weight of about 255, 410 or 435 and applying the resulting terpenoid-containing neutral lipid fraction to soil prior to planting or seeding the soil with sugar beet in an amount effective to enhance the hatching of cysts and eggs of said nematodes.

2. A method in accordance with claim 1 wherein the nematodes of the genus *Heterodera* are selected from the group consisting of the species *Heterodera schachtii*, *Heterodera rostochiensis*, *Heterodera glycines*, *Heterodera trifolii* and *Heterodera avenae*.

3. A method in accordance with claim 1 wherein the lipid fraction is applied by spraying a solution or suspension thereof onto the soil.

4. A method in accordance with claim 1 wherein said lipid fraction is applied to the soil be applying a solution or suspension thereof to the soil beneath the surface thereof.

* * * * *